United States Patent [19]

Peltonen et al.

[11] Patent Number: 4,498,338

[45] Date of Patent: Feb. 12, 1985

[54] PROCEDURE AND MEANS FOR MEASURING THE COAL CONTENT IN QUICK ASH

[75] Inventors: Eero Peltonen, Espoo; Aarni Somerikko, Helsinki; Timo Viitanen, Espoo, all of Finland

[73] Assignee: Kajaani Oy, Finland

[21] Appl. No.: 461,033

[22] Filed: Jan. 26, 1983

[30] Foreign Application Priority Data

Feb. 1, 1982 [FI] Finland .................................. 820307

[51] Int. Cl.³ ............................................. G01N 27/22
[52] U.S. Cl. ................................. 73/432 R; 324/61 R
[58] Field of Search .......... 73/432 R, 432 CR, 432 Z; 324/61 R

[56] References Cited

FOREIGN PATENT DOCUMENTS 2235037 2/1974 Fed. Rep. of Germany .
2412165 9/1975 Fed. Rep. of Germany .

Primary Examiner—Stephen A. Kreitman
Assistant Examiner—Tom Noland
Attorney, Agent, or Firm—Andrus, Sceales, Starke & Sawall

[57] ABSTRACT

A procedure and an apparatus for continuously measuring the coal content of quick ash, ash being fed through a measuring chamber (1), through between measuring capacitor plates (2), the change of capacitance caused by the coal being measured, and a measuring signal being formed which characterizes the coal content of the ash.

14 Claims, 11 Drawing Figures

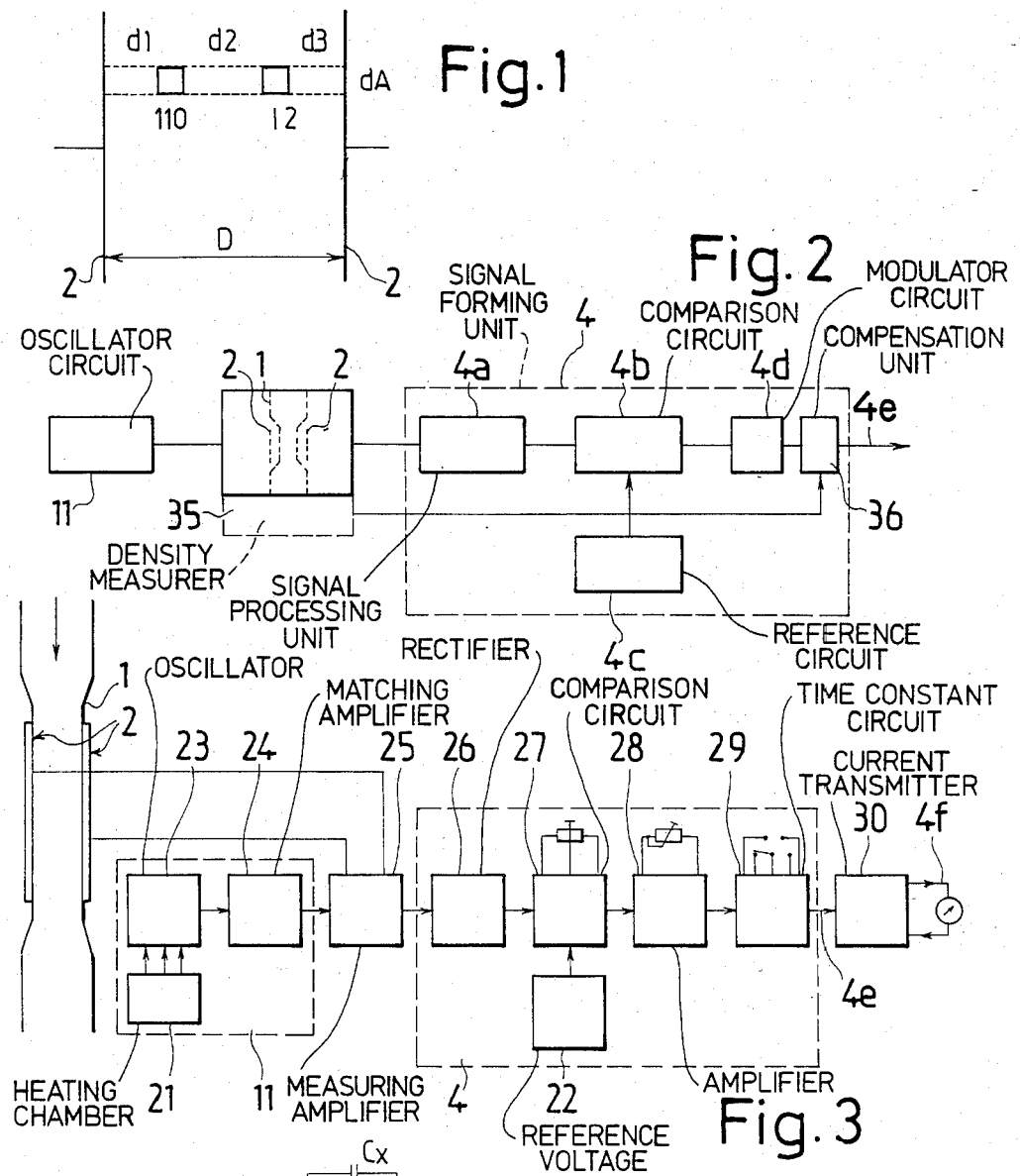
Fig. 1
Fig. 2
Fig. 3
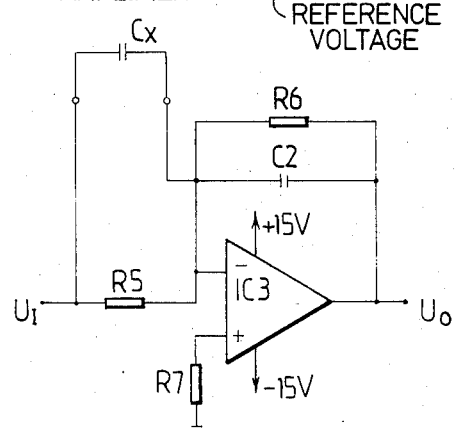
Fig. 4

PROCEDURE AND MEANS FOR MEASURING THE COAL CONTENT IN QUICK ASH

SUMMARY OF THE INVENTION

The present invention concerns a procedure and means for continuously measuring the coal content in quick ash. The procedure and the means are intended for determining the quick ash, particularly in that from a coal-operated power plant, the coal content, i.e., the content of unburned fuel contained in the quick ash.

BACKGROUND OF THE INVENTION

The quick ash from a coal-operated power plant boiler contains a plurality of components, the main part thereof constituted by $SiO_2$, $Al_2O_3$, $Fe_2O_3$, CaO, MgO, and combustible substances. The content of combustible substances, that is mainly coal, in the quick ash may vary within wide limits (0.5 to 20%), depending e.g. on the coal quality, on the condition of the grinders used in comminuting the coal and the adjustment of burners, on the design of the boiler, and on the amount of combustion air. It may be said in general that the quantity of unburned fuel in the quick ash tells about how incompletely/completely the combustion in the boiler takes place. The coal losses, that is the coal that is lost along with the ash, may involve even quite spectacular costs. For instance, in a 500 megawatt power plant (running period 6000 hrs per annum, consumption ratio 2.6, coal price U.S. $60 per ton) the annual expenditures for fuel are about $60 million; and a 1% coal loss, which is equivalent to about 10% coal content in the quick ash, amounts to $0.6 mill. at annual level.

Furthermore, it is substantially important to monitor the coal content of quick ash also in view of the useful applications to which the ash may be put. Quick ash with excessively high coal content is not usable for instance in light-weight gravel production, nor as a constituent in mortar, in cement, etc. In addition, the variation of this coal content restricts the use of quick ash in brick production, as a raw material for autoclaved products, etc.

It is present practice to analyze the quick ash of coal-operated power plants in service laboratories, by analytical methods. The results are usually not obtained until several hours after sampling. It is therefore hardly possible to use the numerical values of the coal losses thus obtained as any kind of guiding values in the control of the combustion process, nor to the purpose of adjusting the coal losses to be at desired level.

The object of the present invention is to eliminate the drawbacks mentioned. A particular object of the invention is to provide a procedure and apparatus for measuring the coal content of quick ash, continuously or periodically, so that the measured values may be employed in process control to regulate the coal losses to be at a desired level, and towards supervision of the combustion means functioning and towards quality control of the ash produced in the combustion, for instance of ash that is meant to be sold.

Regarding the features which are characteristic of the invention, reference is made to the claims section.

DESCRIPTION OF THE DRAWINGS

The invention is described in the following in detail with the aid of embodiment examples, with reference to the attached drawings, wherein:

FIG. 1 presents a schematic diagram illustrating the principle of measurement of the invention, FIG. 2 presents the apparatus according to an embodiment of the invention, in the form of a principle block diagram, FIG. 3 shows the detailed block diagram of the apparatus of the invention, FIGS. 4–5 show the circuit diagram of blocks 12 and 27, respectively, in the apparatus of FIG. 3.

DESCRIPTION OF THE ILLUSTRATED EMBODIMENT

Figure 5:
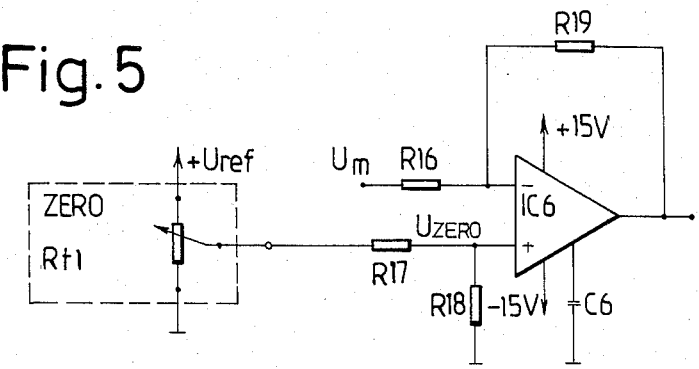

The invention is based on the fact that the coal that has remained unburned, contained in the quick ash, is a good conductor of electricity. The measuring element is a capacitor, the quick ash being fed into the field between its electrodes. In FIG. 1 is shown the arrangement of the measurement, in simplified form. The space between the capacitor plates 2 has been filled with quick ash, which has the dielectric constant $E_t$. Let us consider one differential capacitor composed of the capacitor plate areas dA, spaced by the distance D, and by the ash therebetween, which in the exemplary case of FIG. 1 contains two coal particles (or part of them). The coal particles 110 and 12 have the thickness $l_1$ and $l_2$, respectively, and the coal particles are assumed to be perfect conductors.

The capacitance dC of the differential capacitor corresponding to the volume element $dA \times D$ is found in this case by evaluating the series connection of three capacitors. In the general case, with coal particles numbering N in the given volume element, dC is found by the formula:

$$dC = E_t \frac{dA}{\sum\limits_{1}^{N} d_i} = E_t \frac{dA}{D - \sum\limits_{1}^{N} l_i} \qquad (1)$$

Denoting $$\sum\limits_{1}^{N} l_i = L,$$

from this is further obtained:

$$dC = \frac{E_t}{D} \frac{dA}{D - \frac{L}{D}} \qquad (2)$$

Integrating over the total area A of the capacitor, and assuming that L is constant, the total capacitance is found to be:

$$C = \frac{E_t A}{D} \cdot \frac{1}{1 - \frac{L}{D}} = C_o \frac{1}{1-p} \quad (3)$$

where $L/D = p$ = volume proportion of coal between the capacitor plates, and $C_o$ is the capacitance corresponding to zero ash (implying quick ash in which the coal content is = 0). If p is much smaller than 1, as it mostly is in practice, the following approximate formula is found for C:

$$C \approx C_o(1+p) \quad (4)$$

in other words, the capacitance of the capacitor is an almost linear function of the volume porportion of coal.

It is seen on examination of equations (1) and (3) that the residual coal in the quick ash has a similar effect on the capacitance to that of any kind of electric conductor interposed between the plates. Effectively, it kind of shortens the distance D between the capacitor plates by the thickness L of a conductive layer equivalent to the volume proportion p.

The measurement is also influenced by the packing density of the ash, in other words by the air remaining between ash particles. Endeavours are made to minimize the variations in packing density during the measurement by means of a sample flow which is regulated or continuously controllable e.g. in accordance with the loading of the power plant, and by means of vibrators by which the amount of ash flowing freely into the measuring chamber is regulated and the flowing of the ash in the sample flow line and in the measuring chamber is promoted.

Figure 7:
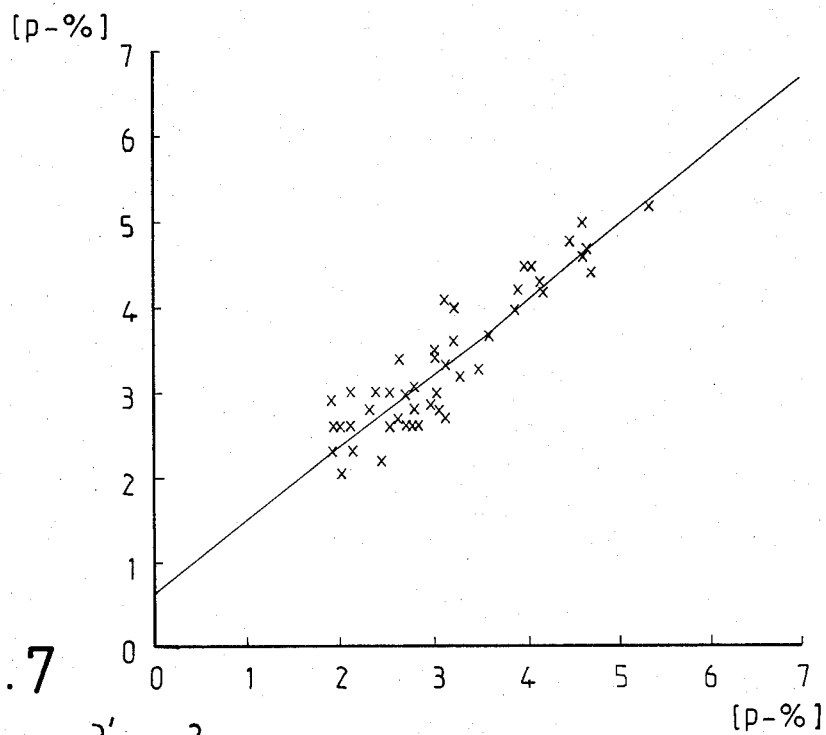

In FIG. 7 is shown the correlation which exists between the results of measurements made by the procedure of the invention and simultaneously made laboratory analyses. On the horizontal axis have been plotted the ignition losses found in laboratory analysis, in percent by weight, that is the coal content values, while the vertical axis indicates the results of measurement obtained by the procedure of the invention.

In FIGS. 2-3 is shown the mode of forming the measuring signal in the procedure of an embodiment of the invention, as a principle block diagram, in a measuring unit according to the invention. In the procedure, ash is supplied substantially at constant density, continuously, through the measuring chamber 1, through between the measuring capacitor plates 2. The change caused by the coal contained in the ash in the capacitance of the capacitor is measured, and a measuring signal consistent with said change of capacity is formed, which signal will then characterize the coal content of the ash.

In FIGS. 2-3, an alternating voltage is formed in the oscillator circuit 11 and conducted to the electrodes 2 of the capacitor belonging as an essential part to the measuring element, and amplifier, 25. Ash is continuously led through the measuring chamber 1 through the electric field established by the capacitor. From the capacitor, the measuring signal is conducted to a calibrated measuring signal forming unit 4; that is, as shown in FIG. 2, to a signal processing unit 4a, a comparison circuit 4b and a modulator circuit 4d, the measuring signal processed in the comparison circuit 4b is compared to a reference voltage formed in the reference voltage forming circuit 4c. In FIGS. 2-3, the output 4e of the measuring signal forming unit 4 is a linear standard meassage. The measuring signal thus obtained from the capacitor 2 and characterizing the coal content of the ash flowing through the chamber 1 is amplified, rectified and converted into a current signal, which may be connected to any desired output device or, for instance, connected to control the coal burning process.

In FIG. 3, the calibrated oscillator circuit 11 comprises e.g. a conventional sine oscillator 23, disposed for instance in a heating chamber 21 in order to stabilize the output voltage in case the ambient temperature changes, and a matching amplifier 24 for buffering the output voltage.

FIG. 4 shows the circuitry, in one embodiment, of the measuring element 12, for instance a conventional measuring amplifier. In FIG. 4, the voltage gain of the micro-circuit IC3 depends on the capacitance of the measuring electrodes, that is of the measuring capacitor 2, in other words, on the coal content of the ash under measurement. The gain of the amplifier IC3 is the ratio between the impedance formed by the capacitor C2 and the impedance which is formed by the capacitance of the measuring electrodes and wiring. Hereby the amplifier's output voltage $U_o$ is directly proportional to the capacitance $C_x$ that is being measured, or:

$$U_0 = C_x U_i / C_2,$$

where $U_i$ is the alternating voltage formed by the oscillator circuit 11.

In FIG. 3, the signal obtained from the measuring amplifier 25 has been conducted to the rectifier 26, for instance a conventional full-wave rectifier, in order to rectify the measuring signal. The rectified measuring signal from the rectifier 26 is compared in the comparison circuit 27, e.g. a ZERO amplifier (FIG. 5), with the reference voltage formed in a reference voltage source 22. As shown in FIG. 5, the comparison circuit comprises a subtraction element, i.e., an amplifier IC6 performing the zero point shift of the measuring signal by subtracting the measuring voltage $U_m$ from the reference voltage $U_{zero}$ obtained from the reference voltage source 22. The signal characterizing the coal content of the ash, derived from the comparison circuit 27, is further conducted, as shown in FIG. 3, over an amplifier 28 (SPAN amplifier) and further through a time constant circuit 29 to a current transmitter 30, where the processed measuring signal 4e obtained from the measuring capacitor 2 has been arranged to control the output signal 4f, in other words, the current transmitter operates as a voltage-controlled current generator controlled by the measuring signal and from which the standard message 4f is obtained.

Figure 6:
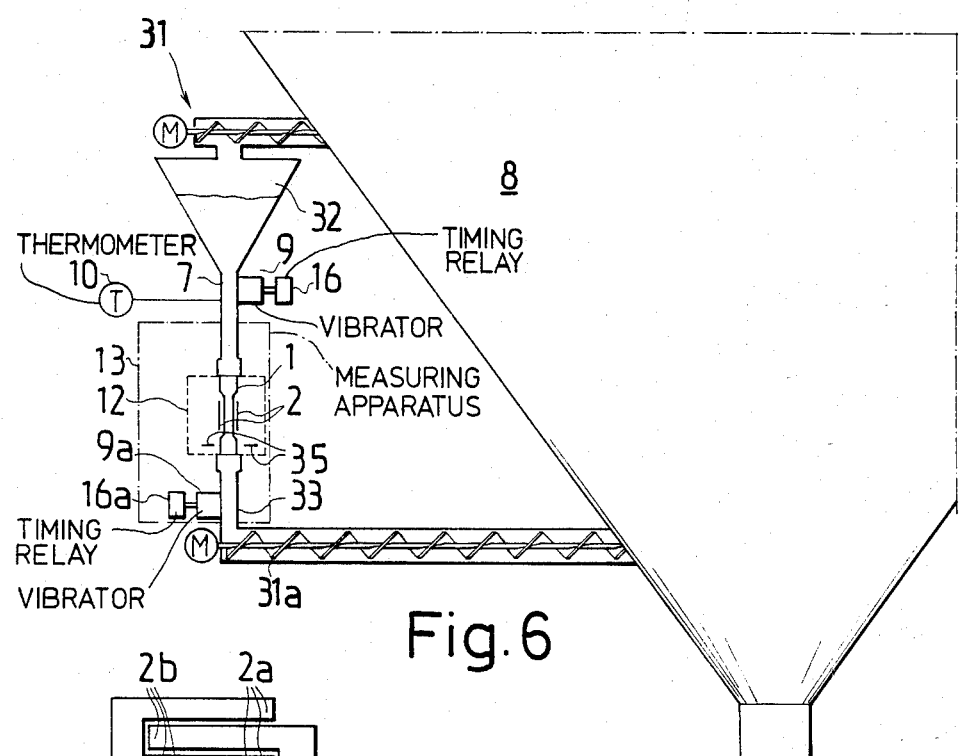
FIG. 6 shows an apparatus according to the invention, connected in conjunction with the quick ash collecting funnel under an electric filter, FIG. 7 displays the correlation between the results of measurement obtained by the method of the invention and laboratory analyses.

In FIG. 6 is seen the measuring equipment 13 installed in conjunction with the ash collector funnel under the electrostatic flue gas filter in a coal-operated power plant.

The measuring apparatus 13 comprises a measuring element 12 with vertical measuring chamber 1 confined by the side walls 3. The ash has been arranged to flow freely into the chamber 1 from the ash line, that is, transported by the screw conveyor 31, from the silo 8 to the funnel 32 placed above the chamber 1, and thence through a vertical ash tube 7 into the chamber, said tube 7 connecting the chamber to the funnel. In conjunction with the lower end of the chamber 1 and with tube 33 has been disposed a vibrator 9a, governed by a timing relay 16a, for conducting the ash through the chamber 1 and further to a screw conveyor 31a, which empties ash from the tube 33 back into the silo 8. The ash tube 33 conducting ash off from the chamber, that is into the silo 8, is provided with a screw conveyor 31a, the drive means of the latter, for instance a motor, being provided with speed adjustment so that the transporting rate of the conveyor, and thus the ash flow through the chamber 1, is adjustable. In the embodiment depicted, a vibrator 9 governed by a timing relay 16 has been attached to the ash tube 7, this vibrator being disposed to shake ash from the funnel into the ash tube and further into the measuring chamber.

When the apparatus is in operation, a side flow will go from the ash accumulating in the silo 8, to the ash funnel 32 and further to the measuring chamber 1. The ash fills the tube and chamber, this being full of ash at all times, ash density in the chamber substantially constant, and flows through the electric field of the chamber's capacitor plates at a constant flow rate while the vibrator 9a is working. At the same time, more ash flows into the ash tube, whereby the ash flow passing through the chamber and the density of the ash are constant on the average.

The ash tube may be provided with a thermometer 10, for instance to indicate plugging of the ash tube or for another reason. When the temperature variations cease in the ash tube 7 and the temperature begins to go down in the ash tube, this indicates plugging of the ash tube.

In FIG. 6 is further seen as ash density measuring means 35, which has been disposed in conjunction with the measuring apparatus 13 to measure the density of the ash passing through the measuring chamber 1. The measuring means 35 can be a density measuring apparatus of any kind whatsoever, for instance a scales means for determining the specific gravity of coal, known in itself in the art, or for instance an electrical measuring means. The measuring means 35 is to advantage arranged to apply a correction to the signal derived from the capacitor 2 and/or to the measuring signal 4e, for instance in the manner shown in FIG. 2 with the aid of a particular compensation unit 36. The measuring means 35 may be placed e.g. before the measuring chamber 1 in conjunction with the ash tube 7, or in conjunction with the measuring chamber 1, or in conjunction with the ash tube 33 carrying off ash from the measuring chamber 1.

Figure 8:
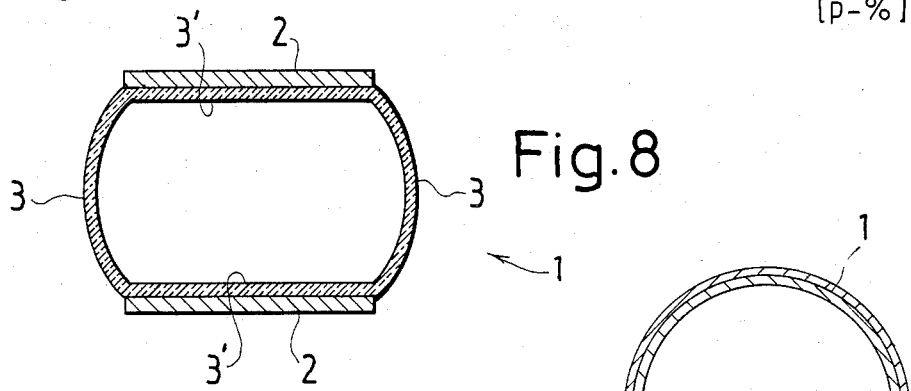
FIG. 8 shows the cross section of the measuring chamber belonging to an apparatus according to the invention.

In FIG. 8 is seen, in horizontal section, the measuring chamber belonging to an apparatus according to the invention. The chamber 1 is a substantially vertical, tubular flow-through member confined by lateral walls 3. The chamber has been made e.g. of glass. The tubular chamber has been flattened in lateral direction so that two mutually opposed walls 3' are planar.

Figure 9:
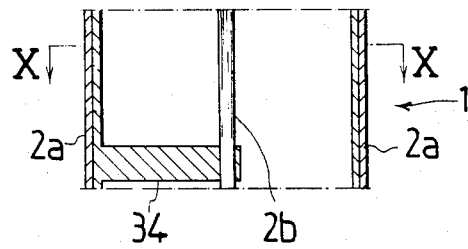
FIGS. 9–10 show sections of another measuring chamber according to the invention.
Figure 10:
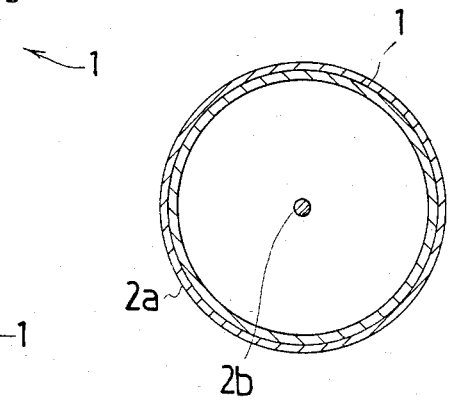

The capacitor plates 2 have been affixed outside said opposed walls and against them, and substantially parallel to each other, so that the changes in the capacitor's capacitance caused by the coal contained in the ash conducted with substantially constant density through the chamber between said plates are measurable by the aid of the capacitor In FIGS. 9 and 10 is depicted the measuring chamber 1 according to an advantageous embodiment of the invention, in longitudinal section and in transversal section. The chamber 1 has a substantially circular cross section. The electrodes of the capacitor 2, that is the capacitor plates 2a and 2b, have been devised in the shape of a centric cylinder and the pin-shaped axis of said cylinder. It is hereby possible to minimize the stray capacitances established between the electrodes and even virtually to eliminate them, owing to the circular symmetric design of the capacitor which is employed. In this embodiment, the central electrode 2b may be supported in position e.g. by the aid of a support arm 34 attached to the chamber's side wall and/or by one or several particular supports placed below or above the chamber. The central electrode may in such case be connected to the measuring apparatus by means of a lead attached to the supporting means.

Figure 11:
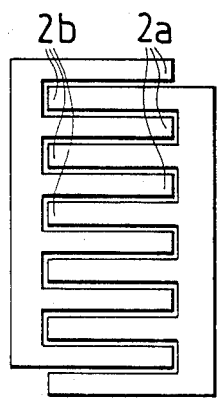
FIG. 11 presents, in elevational view, the electrodes of the capacitor in a third embodiment of the invention.

In FIG. 11 is seen the capacitor according to a favourable embodiment of the invention, where both electrodes 2a and 2b of the capacitor have a finger-like or comb-like shape. The finger-like electrodes belonging to the capacitor are intercalated, and they have been installed substantially in the same plane. In this case the ash flow is conducted past the electrodes, that is, through the electric field established by the electrodes.

The embodiment examples are merely intended to illustrate the invention, without in any way restricting it. Embodiments and variants of the invention may vary within the scope of the claims stated below, and thus for instance the equipment according to the invention may comprise, instead of or in addition to the measuring signal processing, comparison, conversion, amplifying etc. circuits presented by way of example in the embodiment examples, any kinds of apparatus used for signal processing in measuring electronics. The site presented above for installation of the measuring means, namely, in conjunction with the ash collecting silo under the electric filter, has mainly the nature of an example. It is thus understood that the means based on the present invention may naturally also be installed elsewhere, for instance to measure quick ash that has been separated from the flue passage by means of an ash separator specifically devised for this purpose, in which case the technical details of the means may differ from what has been presented in the foregoing.

We claim:

1. A method for measuring the coal content of quick ash, comprising the steps of feeding quick ash containing uncombusted coal particles into an electric field established by a pair of spaced electrodes of a capacitor, measuring the change in capacitance of the capacitor, and generating a measuring signal which indicates the coal content of said ash.

2. The method of claim 1 and including the step of maintaining the density of the ash substantially constant during measuring of said capacitance.

3. The method of claim 1 wherein said step of feeding comprises continually passing the quick ash through said electrical field.

4. The method of claim 1 wherein the step of feeding the ash into said electrical field takes place periodically with the length of the period being adjustable.

5. The method of claim 1 and including the step of vibrating the ash to maintain uniform density of said ash.

6. A method for measuring the coal content of quick ash, comprising the steps of continuously feeding quick ash containing uncombusted coal particles into a measuring chamber containing an electric field established by spaced electrodes of a capacitor, measuring the capacitance of the ash being fed through said chamber, generating a measuring signal indicating the coal content of the ash, comparing the measuring signal to a reference signal to generate an output signal proportional to the difference between the measuring signal and a reference signal, and utilizing the output signal to control the feed of ash into said measuring chamber.

7. An apparatus for measuring the coal content of quick ash, comprising a measuring chamber, a capacitor disposed in the measuring chamber and including a pair of spaced electrodes, means for continuously feeding quick ash containing uncombusted coal particles through said measuring chamber, means for measuring the capacitance of the ash and generating a measuring signal proportionate to the content of coal particles in said ash.

8. The apparatus of claim 7 and including means for maintaining the ash passing through said measuring chamber at a relatively constant density.

9. The apparatus of claim 8 wherein each electrode includes a series of fingers interlaced with the fingers of the other electrode, said ash flowing through the space between the fingers.

10. The apparatus of claim 7 wherein said measuring chamber is disposed substantially vertically, and said apparatus includes discharge conveyor means connected to the lower end of said measuring chamber for removing ash from the lower end of said chamber.

11. The apparatus of claim 7 and including vibrator means for vibrating the ash flowing through the chamber to maintain a substantially constant density for said ash.

12. The apparatus of claim 7 and including weighing means for determining the weight of the ash in the measuring chamber, and compensating means for correcting the measuring signal in accordance with the difference in weight from a reference weight.

13. The apparatus of claim 7 wherein the capacitor comprises a pair of electrodes which are substantially planar and between which the ash flows.

14. The apparatus of claim 7 wherein the capacitor comprises a pair of electrodes, one of said electrodes being annular at least in part and the second of said electrodes being disposed centrally with reference to said annular electrode, said ash flowing between said electrodes.

* * * * *

UNITED STATES PATENT AND TRADEMARK OFFICE
CERTIFICATE OF CORRECTION

PATENT NO. : 4,498,338

DATED : February 12, 1985

INVENTOR(S) : EERO PELTONEN ET AL

It is certified that error appears in the above-identified patent and that said Letters Patent is hereby corrected as shown below:

Cover Page at [56] After "References Cited" insert:

---UNITED STATES PATENTS

| | | | |
|---|---|---|---|
| 2,540,146 | 1/1951 | Stober | 324/61RX |
| 2,726,366 | 12/1955 | Rogers | 324/61RX |
| 3,760,267 | 9/1973 | Williams | 324/61R |
| 4,319,491 | 3/1982 | Christoffersen et al | 324/61RX |
| 4,403,191 | 9/1983 | Sutake | 324/61RX |

FOREIGN PATENTS

| | | | |
|---|---|---|---|
| 909,021 | 9/1972 | Canada | 324/61R |
| 508,512 | 8/1929 | Fed.Rep.of Germany | 324/61R |
| 273,489 | 9/1970 | U.S.S.R. | 324/61R |

UNITED STATES PATENT AND TRADEMARK OFFICE
CERTIFICATE OF CORRECTION

PATENT NO. : 4,498,338

DATED : February 12, 1985

INVENTOR(S) : EERO PELTONEN ET AL

It is certified that error appears in the above-identified patent and that said Letters Patent is hereby corrected as shown below:

OTHER REFERENCES

"Flow Monitor"; RCS Technical Notes No.697, 1-1967, Herbert Bernard Goldman et al; in 324/61R "Factors Affecting Woodchip Moisture Measurement:" Paper Trade Journal, 7-1974; pp.21-24; F.K. Preiklschet et al; in 324/61R--

Signed and Sealed this

Twenty-fourth Day of September 1985

[SEAL]

Attest:

Attesting Officer

DONALD J. QUIGG

Commissioner of Patents and Trademarks—Designate